(12) United States Patent
Guerra

(10) Patent No.: US 8,757,161 B2
(45) Date of Patent: Jun. 24, 2014

(54) TRACHEOSTOMY APPARATUS AND DEVICE

(75) Inventor: Romano Guerra, Monfalcone (IT)

(73) Assignee: Romano Guerra, Monfalcone (IT)

( * ) Notice: Subject to any disclaimer, the term of this patent is extended or adjusted under 35 U.S.C. 154(b) by 958 days.

(21) Appl. No.: 12/441,815

(22) PCT Filed: Sep. 20, 2007

(86) PCT No.: PCT/EP2007/059956
§ 371 (c)(1),
(2), (4) Date: Mar. 18, 2009

(87) PCT Pub. No.: WO2008/034872
PCT Pub. Date: Mar. 27, 2008

(65) Prior Publication Data
US 2010/0012130 A1    Jan. 21, 2010

(30) Foreign Application Priority Data

Sep. 22, 2006   (IT) .............................. GO2006A0002
Sep. 22, 2006   (IT) ............................. GO20060001 U

(51) Int. Cl.
*A61M 16/00*    (2006.01)
*A61M 16/04*    (2006.01)

(52) U.S. Cl.
CPC ................................. *A61M 16/0434* (2013.01)
USPC ................................................ 128/207.15

(58) Field of Classification Search
CPC .......... A61M 16/034; A61M 16/0465; A61M 16/0472; A61M 2016/0445; A61M 2016/0447; A61M 2016/0459
USPC ............. 128/207.14, 207.15, 207.16, 207.17, 128/207.18, 200.24, 207.29; 606/191–200; 604/401–106
See application file for complete search history.

(56) References Cited

U.S. PATENT DOCUMENTS

| | | | | | |
|---|---|---|---|---|---|
| 3,087,493 | A | * | 4/1963 | Schossow | 128/207.15 |
| 3,610,247 | A | * | 10/1971 | Jackson | 128/207.15 |
| 4,471,776 | A | | 9/1984 | Cox | |
| 4,946,440 | A | * | 8/1990 | Hall | 604/164.09 |
| 5,020,534 | A | * | 6/1991 | Pell et al. | 128/207.15 |
| 5,108,414 | A | * | 4/1992 | Enderle et al. | 606/193 |
| 5,176,619 | A | * | 1/1993 | Segalowitz | 600/18 |
| 5,720,726 | A | * | 2/1998 | Marcadis et al. | 604/103.08 |
| 6,129,737 | A | * | 10/2000 | Hamilton et al. | 606/194 |
| 8,434,487 | B2 | * | 5/2013 | Nelson et al. | 128/207.15 |
| 2004/0024291 | A1 | * | 2/2004 | Zinkel | 600/218 |
| 2004/0255954 | A1 | | 12/2004 | Zgoda et al. | |

FOREIGN PATENT DOCUMENTS

| | | | | |
|---|---|---|---|---|
| EP | 784989 | A2 * | 7/1997 | A61M 16/04 |
| EP | 1044701 | A | 10/2000 | |
| WO | 2005/094926 | A | 10/2005 | |

* cited by examiner

*Primary Examiner* — Lynne Anderson
*Assistant Examiner* — Bradley Philips
(74) *Attorney, Agent, or Firm* — Cooper Legal Group, LLP

(57) ABSTRACT

A device and a method for the percutaneous placement of a tracheostomy tube composed of a handle, an inflatable balloon having a reversed truncated cone shape, a tube to inflate the balloon and another to contain a wire guide, a plastic structure in the middle between the balloon and the handle made of laminar elements to strengthen the apparatus movements of the handle transmitted to the tube and the balloon. Following placement of the tracheal tube, the balloon is deflated and the apparatus or device withdrawn.

12 Claims, 8 Drawing Sheets

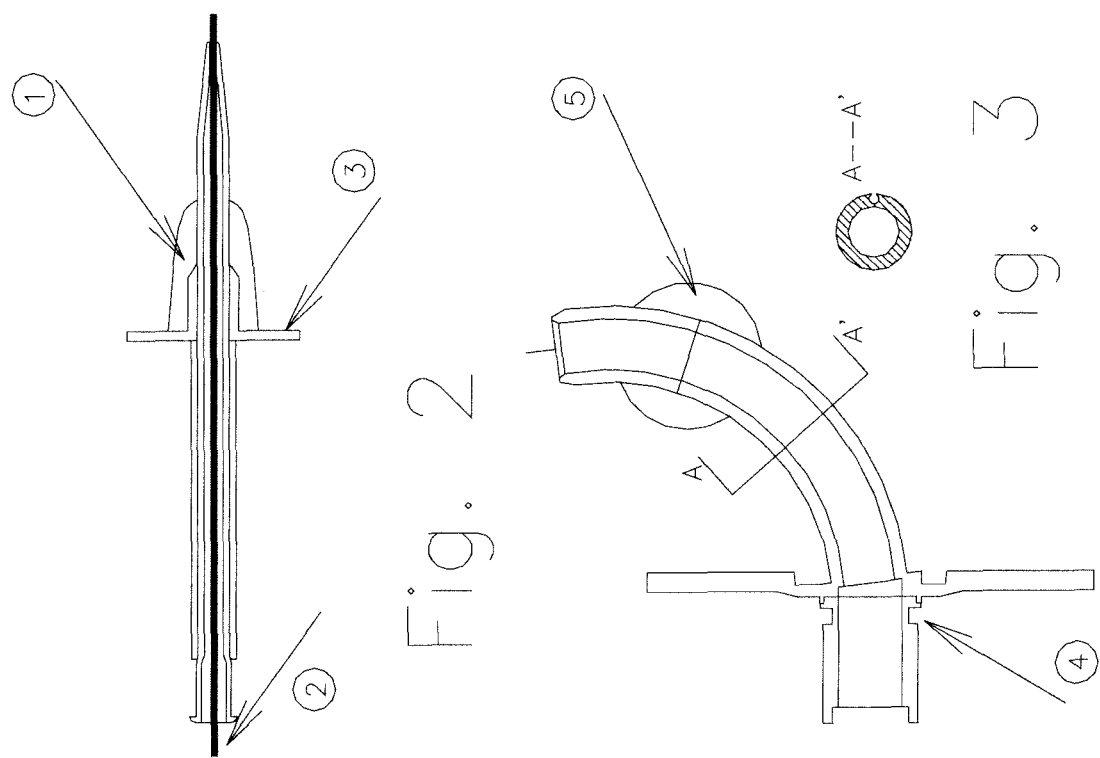

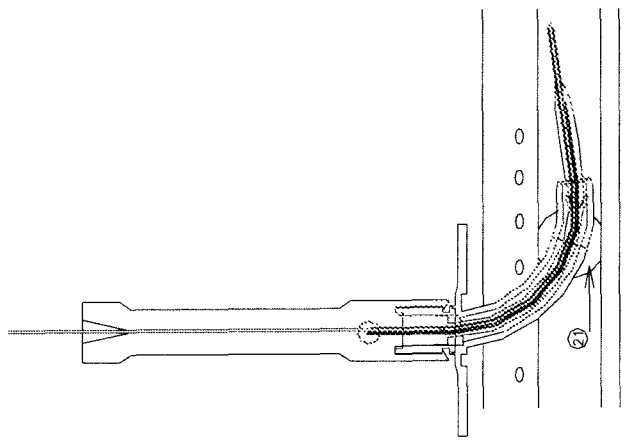
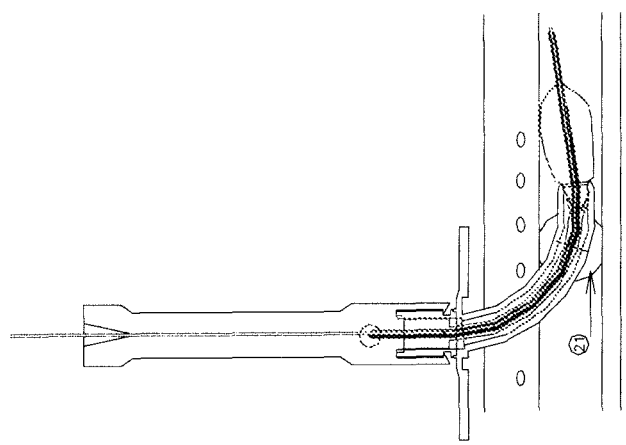 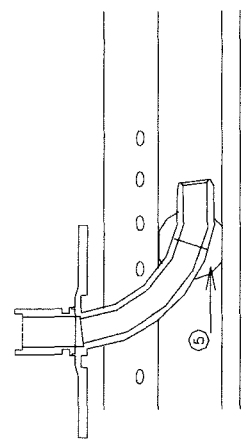
Fig. 6

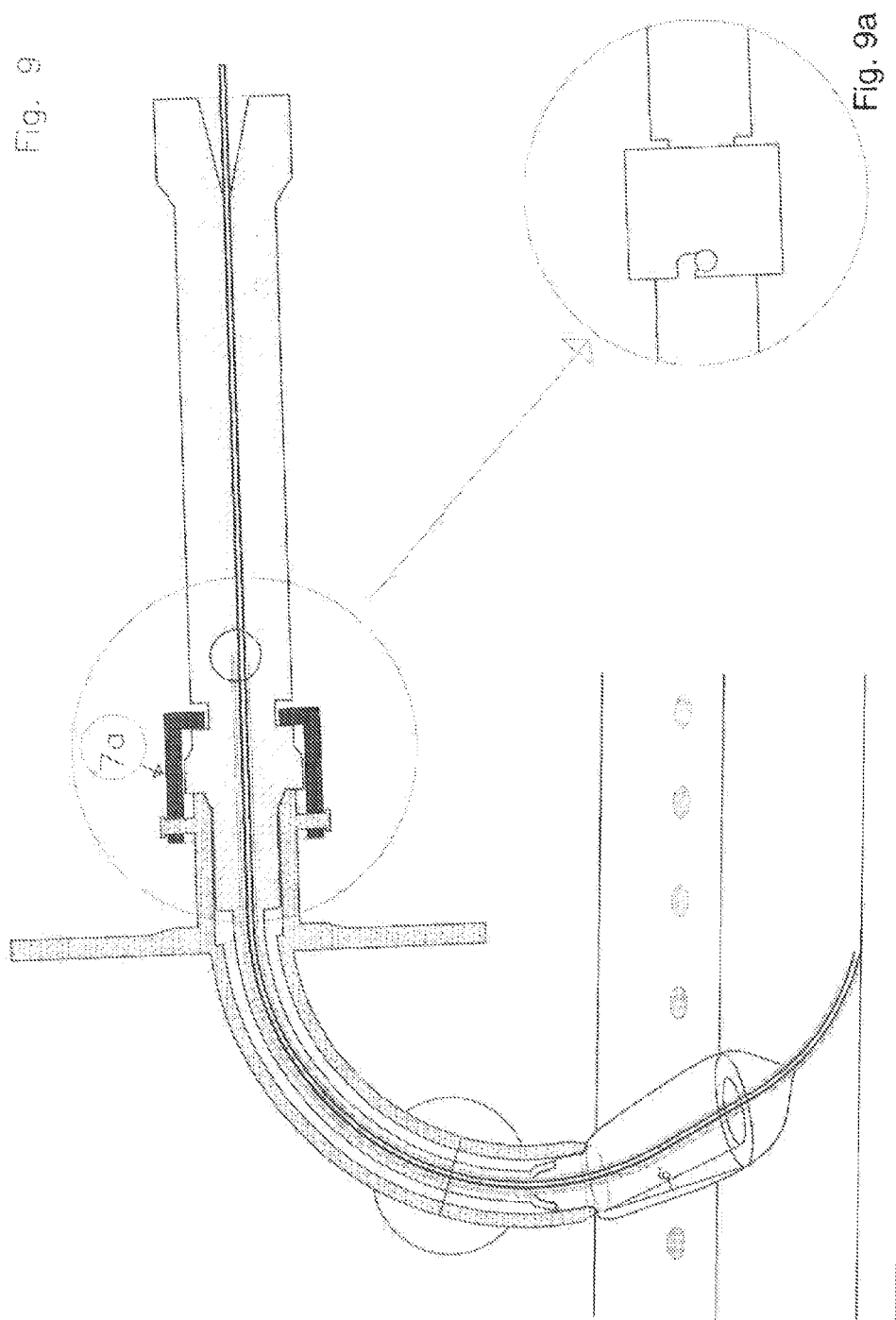

TRACHEOSTOMY APPARATUS AND DEVICE

TECHNICAL FIELD

The present invention relates to a device to open a bore in the tracheal wall of a patient and to introduce a tracheal tube in the trachea in a non traumatic way. The invention also relates to a method for placing a tracheostomy tube in the trachea of a patient. More specifically, the invention relates to a dilating and introducer balloon, tracheal tube and handle assembly for use in the percutaneus insertion of a tracheostomy tube in the trachea of a patient.

BACKGROUND

Currently several more or less invasive devices and methods to perform a tracheostomy are available on the market and in literature.

The oldest and most used method is represented by the procedures of surgical trachestomy or cricothyroidotomy. The method consists in forming a surgical opening between the tracheal rings using surgical and traumatic tools like a scalpel and a dilator pincer. All this requires the activation of a surgical team, a sterilized environment and complex structures not always easy to find in emergency situations. The surgical opening of the trachea is complex, traumatic, requires the incision with a scalpel, opening an extended breach, tying the blood vessel, often a copious bleeding, a long anaesthesia, potential infective complications, and has a duration of about 30 minutes. This method can be preferred in some situations, for instance patients with a neck anatomy of difficult approach, but is not easy to be adopted in emergency situations, and moreover is very expensive for the tools and the personnel required.

In order to overcome these drawbacks, in the last years new tracheostomy techniques have been developed to place a tracheostomy tube with micro invasive techniques that allow not to use the classic surgical tracheostomy.

One of these techniques requires the use of dilator tools made of water-repellent plastic material. These dilators of increasing dimensions are introduced between the first tracheal rings through a small aperture obtained with a thick needle or with a scalpel. Then a wire guide is inserted to provide guidance for the insertion of the tubes or the dilator, to obtain a breach of size sufficient to allow placement of the tracheal tube. This technique requires a significant force on the longitudinal axis, and towards the posterior tracheal wall to be applied, in order to advance the dilators and to enlarge the breach to a size sufficient to allow placement of the tracheal tube.

The drawbacks of this technique are the long sequence of manipulations, a significant manual effort, the potential damages to the posterior tracheal wall produced by the rubbing of dilators during the advancing phase, the tissue separation in longitudinal direction, especially when using only one dilator.

One technique uses a curved cone shape dilator, similar to a rhinoceros horn, with increasing diameter from the distal to the proximal base; this requires a further step and an additional device to be placed inside the tube to help maintaining the tissues dilated and to allow overcoming obstacles.

Another method, similar to the previous one in the preparation and the use of a wire guide and as means for dilation a plastic tool provided on the distal portion of a screw thread that continues in the proximal direction with an increasing diameter up to a size sufficient for the tube to be inserted. The device inserted through a wire guide allows opening a breach between the tracheal rings with circular clockwise movements. This method carries on the limits of the previous one and can create an irregular breach with following protrusive scar on the tracheal lumen. Advantages of this technique are the possibility to keep the patient intubated and ventilated during the all the phases of dilation and placement of the tracheostomy tube.

Is also available a device that uses in alternative to the dilators an armed tracheal tube with a cuff at the distal end of a metallic sharp pointed groin. The metallic groin is tied to a metallic thread coming to the mouth from backwards, passed across the tracheal rings with a needle. Dragging the metallic wire with a significant force, the sharp pointed groin, trailing the tracheostomy tube will open a breach from inside the trachea outwards. This is a complex method with many difficulties, requiring a high manual skill and the need to perform some phases of the work very quickly as sometimes the patient cannot be intubated and ventilated.

In the recent years many devices have been designed for the percutaneus introduction of tracheal tubes using a dilator balloon in the dilation phase. However the insertion of the tracheal tube still represents a problem. Usually catheters with dilator balloon available in the market and used in angioplasty are used. The profile of these balloons doesn't allow friction to decrease when advancing in the trachea as the diameters remain fixed from the proximal to the distal end apart the tapering to tie to the wire guide (U.S. Pat. No. 7,036,510, US2005/094926, EP 784989). Moreover, no attention is given to the positioning of the inflation lumen in the dilator balloon, putting it also in proximal position. This generates the risk that during inflation the balloon is pushed backwards, when the inflated part is not inside the trachea yet.

Another device (EP 784989, U.S. Pat. No. 7,036,510) includes a balloon used only as a dilator, and not as introducer. The concept of handle is not developed to get the device easier to be manipulated and able to transmit precisely the thrust needed to introduce the tube, as well as the intermediate part of the device is not developed to grip tightly the tube during the dilation and advancing phases, to have a simple and rapid to be withdrawn once the tracheal tube is placed.

All these techniques require the patient to be intubated and ventilated, under endoscopic control. Then they are not suitable for emergency tracheostomy, namely when it is not possible to intubate the subject, and in cases of unstable cervical rachis fracture.

DESCRIPTION OF THE INVENTION

The author of the instant invention set up an apparatus that is very effective in dilating the tracheal rings, allowing precise device control.

One important innovation of the invention is the shape of the balloon, namely the balloon portion active during the dilation phase is characterized by a reverse truncated cone shape, with its minor diameter adjacent to the tracheal tube and its major diameter distal to it.

This shape results to be optimal for opening the trachea from inside, offering less resistance and then being less traumatic for the tracheal tissues of the patient.

It is therefore an object of the invention a tracheostomy device comprising: a handle (6), an inflating tube (8) and a wire guide tube (13), an intermediate portion (9) to sustain the inflating tube (8) and the wire guide tube (13), a dilating balloon (11), said balloon being inflatable through said inflating tube (12), characterized by the fact that:
a) the balloon (11) has a portion active during the dilation phase characterized by a reverse truncated cone shape, wherein the distal end base diameter is larger than the proximal end base diameter, when said balloon is inflated;

b) the shape of the inflated balloon is tightly connected to the tracheal tube, causing a thrust to move forward the device itself in the trachea;

c) the proximal portion of the inflated balloon is partially inside the tracheal tube, and d) the distal end portion (12) of the inflating tube (8) is connected to the distal portion of the balloon (11).

Preferably the handle (6) in its distal part is hooked to the proximal end of the tracheal tube (4) by a twist-lock connector (7a) or two hooked arms (7).

Preferably the handle handgrip is placed across the device in a "T" shape.

In a preferred embodiment the intermediate portion (9) of the device sustains and carries the tracheostomy tube, more preferably the tracheostomy tube is grip firmly to the device so that the device after the dilation phase is used also as insertion device.

In a preferred embodiment the intermediate portion (9) is curve shaped.

In a preferred alternative embodiment the intermediate portion (22) is straight shaped.

It is within the scope of the invention an apparatus for tracheostomy comprising the device as above disclosed and a small dilator (FIG. 2) to be used for facilitating the introduction of the device comprising at its outer part two opposite scalpel blades (1).

It is within the scope of the invention a method for performing a non traumatic tracheostomy with the apparatus as above disclosed, comprising the steps of:

a) forming a punctured opening in the tracheal wall with a needle;

b) inserting a wire guide through the needle bore and withdrawing the needle;

c) inserting the small dilator according to claim 7;

d) blading along the wire guide across the tracheal wall;

e) inserting the apparatus along the wire guide across the tracheal wall with the tracheostomy tube hooked to the handle and positioning the deflated balloon in the internal wall of the trachea;

f) inflating the balloon, having the inflation start from its distal end of the balloon to get dilation of said punctured opening by the pressure of the inflated balloon on the tracheal wall from inside the trachea outwards;

g) having the tracheal wall dilated, inserting the tracheostomy tube inside the trachea;

h) deflating the balloon and withdraw the apparatus from the tracheostomy tube.

DETAILED DESCRIPTION OF THE INVENTION

The invention will be described with reference to following non limiting embodiments also disclosed in the following figures:

FIG. 2 represents a view of longitudinal section of the small dilator with two small opposite scalpel blades of the apparatus;

FIG. 3 represents a view of longitudinal section of the tracheal tube of the device;

FIG. 6 represents a particular aspect of the inflated balloon using the apparatus of the invention (steps #5 to #7);

FIG. 9 represents a longitudinal view of the device with a twist-lock connector; and FIG. 9a represents a detail view of the twist-lock connector shown in FIG. 9.

The device for the percutaneous placement of a tracheostomy tube is composed in proximal part of a handle (6), in the middle a plastic structure, with laminar elements (9) to strengthen the device itself, containing a balloon inflating tube (8-12) and a wire guide tube (13) and in the distal part, a dilating balloon (11) having a truncated cone shape. Following placement of the tracheal tube, the balloon (11) is deflated and the device withdrawn.

The truncated cone shape inflated balloon (11) is very effective in dilating the tracheal rings, with the distal end diameter larger than the proximal end diameter.

Figure 1:
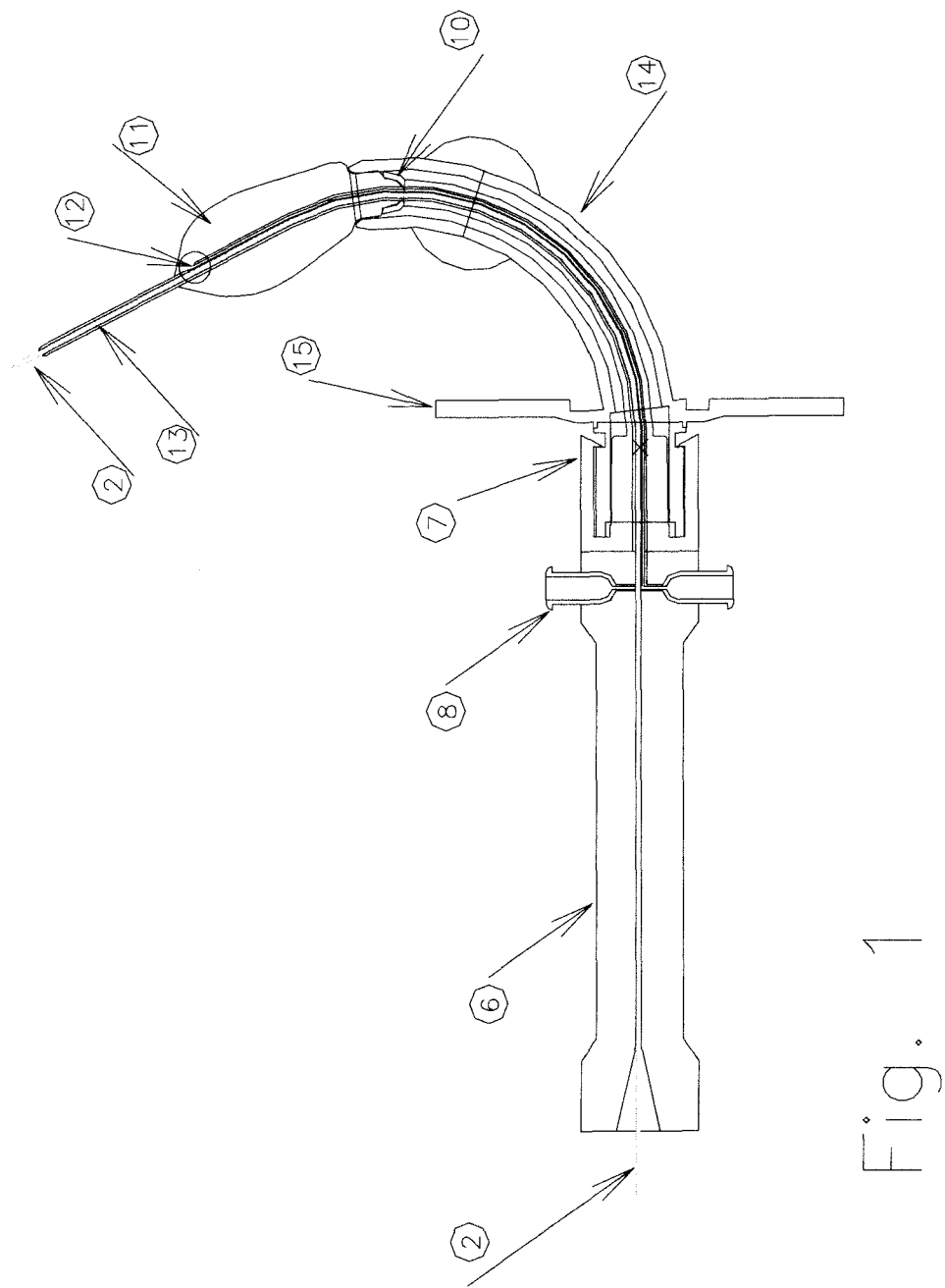
FIG. 1 represents a longitudinal view of the device.
Figure 4:
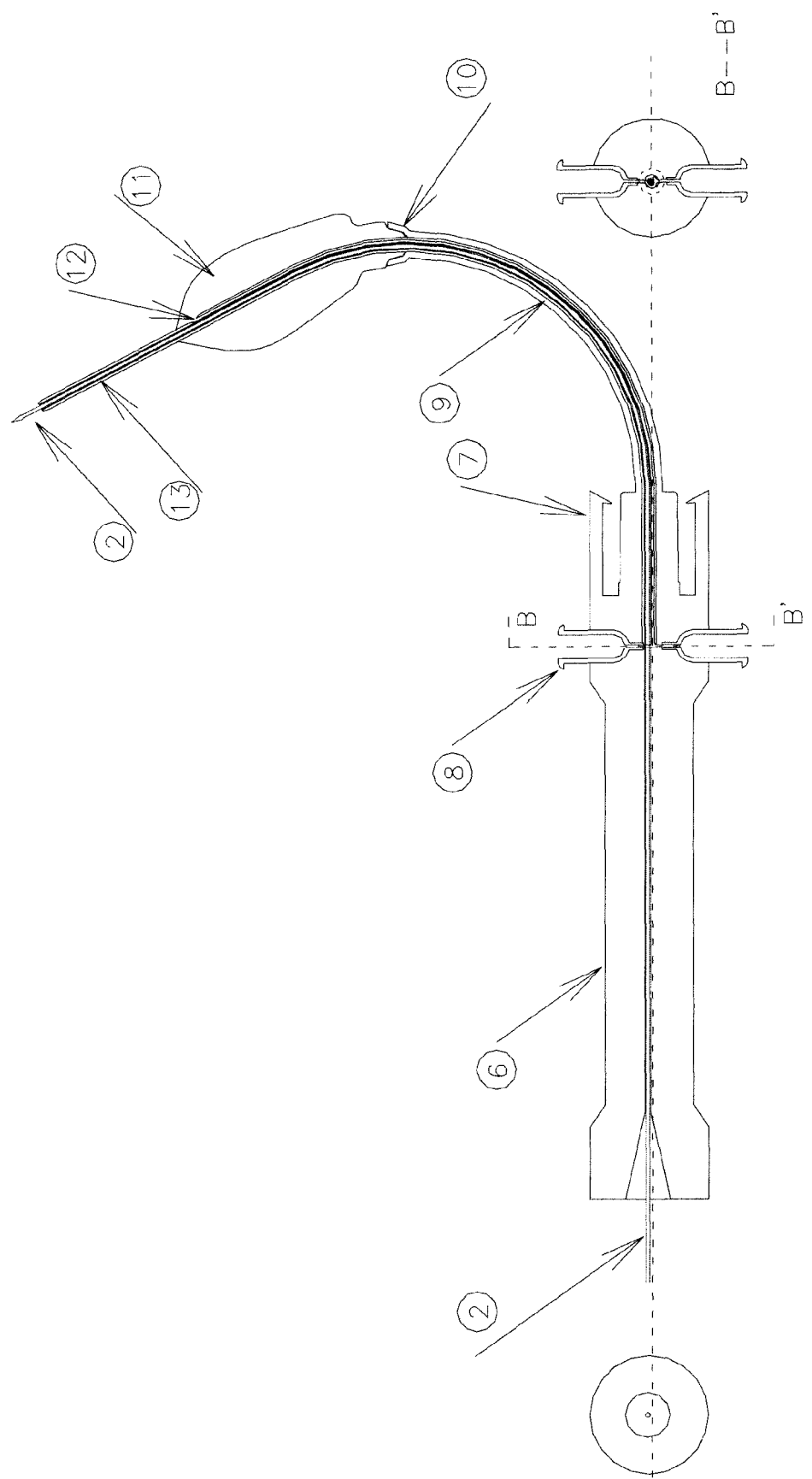
FIG. 4 represents a view of longitudinal section of the device.

The inflating tube (8-12) ends in the balloon distal end so that during the inflation the balloon (11) dilates the trachea from inside and causes a force to enter the tracheal tube in the trachea aperture; its proximal portion diameter just outside the tracheal tube in distal direction is some millimeters larger than the tracheal tube (FIG. 1). The balloon proximal end is inside the tracheal tube so that, when it's inflated rigidly tight together: the balloon, the tracheal tube and the handle, allowing precise device control (FIG. 1).

The device is made by plastic material provided with handle in the proximal end, has a tapered intermediate part (9) made of a flexible material to contain the inflating tube and tube for wire guide and sustain the tracheal tube, distal part, external to the tracheostomy tube (13-11), provided with a dilator balloon (11).

The handle allows to manipulate the device, it's provided of two Luer adapters (8) for the balloon inflation tube. This allows to use both hands right or left, and is capable to connect a unidirectional Luer valve or a tap (ON-OFF), obtaining both a flexibility in usage and an optimal safety during inflation and deflation.

Moreover the handle is provided of wire guide tube's opening (2). This opening may have Luer adapter (FIG. 8, n.2) to feed oxygen if needed.

The handle is provided with two small flexible hooked arms (7); the hooking with the proximal part of the tube (4) gives robustness to the whole assembly, allowing an easy unhooking after insertion of the tracheal tube. Alternatively screw or twist-lock junctions (7a) can be used.

The handle allows to manipulate precisely the device and the balloon to be inflated with a pistol pump or a screw or piston syringe keeping the hand on the device. This gives stability and allows quicker procedure. For a better ergonomic two options have been designed, the former with the handle parallel to the assembly (FIG. 1-4), the latter one with the handle orthogonal to the assembly (FIG. 8, n6a), to better transmit the effort and control the device.

The intermediate part, whose function is to sustain and to grip firmly the tracheostomy tube (9), has a curved shape to follow the tracheostomy tube and contains the tube for the wire guide (2-13) as well as the balloon inflating tube that continue in the distal end of the device (12); each of the two tubes has a diameter ranging between 2.5 and 3 mms (FIG. 4, B-B' section) and is made of flexible material, like PVC. The structure in the intermediate part is sustained by two laminar elements (9) starting from the handle in the proximal part end ending with a cup adherent to the dilator balloon (10).

The laminar elements (9) are made of plastic material for medical products with the characteristics to maintain a flexibility in transversal direction. They give stability and do not allow longitudinal movements of the intermediate part of the device inside the tube during insertion of the dilator balloon in the small breach along the wire guide.

The cup (10) is an element made by plastic material with diameter slightly smaller than the tube diameter. It has the property to give stability during insertion of the device before inflation.

The distal portion of the device contains a dilator balloon (11), partially (i.e. 1-2 cm) inside the tracheal tube, starting from the cup (10) and having a diameter 1-2 mm larger in the distal direction just outside the tube. The balloon (11), when inflated, seals just beyond the inflating tube (12) with the tube containing the wire guide (13). The dilator balloon has a truncated cone shape (FIG. 7) with its base on the distal end of the balloon and the top adjacent to the tracheal tube, active in dilating the tracheal rings. The length of the balloon depends of sex, age and size of the patient; usually it ranges between 3 and 5 cm.

The width of the balloon varies depending on the tracheal tube dimensions. The tubes available on the market range from n.4 (i.d. 5.0 mm, o.d 9.4 m.m) to n.9 (i.d. 8.9 mm, o.d 13.8 mm.). The width of the balloon is conveniently larger than the external diameter of the tracheostomy tube, i.e. between 1 and 3 mm.

The inflating tube end (12) contained in the balloon has to be close to the distal end of the balloon (11). The dilator balloon during inflation with air or fluids will develop its dilation force starting from the distal end of the balloon, then from inside the trachea outwards, compressing the tracheostomy tube against the peritracheal tissues and the cartilage rings, helping the insertion in the tracheal opening under formation.

The balloon inflation from inside reduces the distance between the distal end of the tracheostomy tube and the tracheal rings (point of greatest dilation effort), resulting in a reduced dilation effort.

This has also the advantage to stabilize the device, allowing the operator to unload the effort on the pistol pump or on the screw syringe during inflation and dilation.

Prior arts solutions inflate the balloon from the proximal end, thus pushing the device backwards, in direction opposite to the insertion.

One important innovation of the invention is the shape of the balloon, namely the balloon portion active during the dilation phase is characterized by a reverse truncated cone shape, with its minor diameter adjacent to the tracheal tube and its major diameter distal to it.

This shape resulted to be optimal for opening the trachea from inside, offering less resistance and then being less traumatic for the tracheal tissues of the patient.

Figure 7:
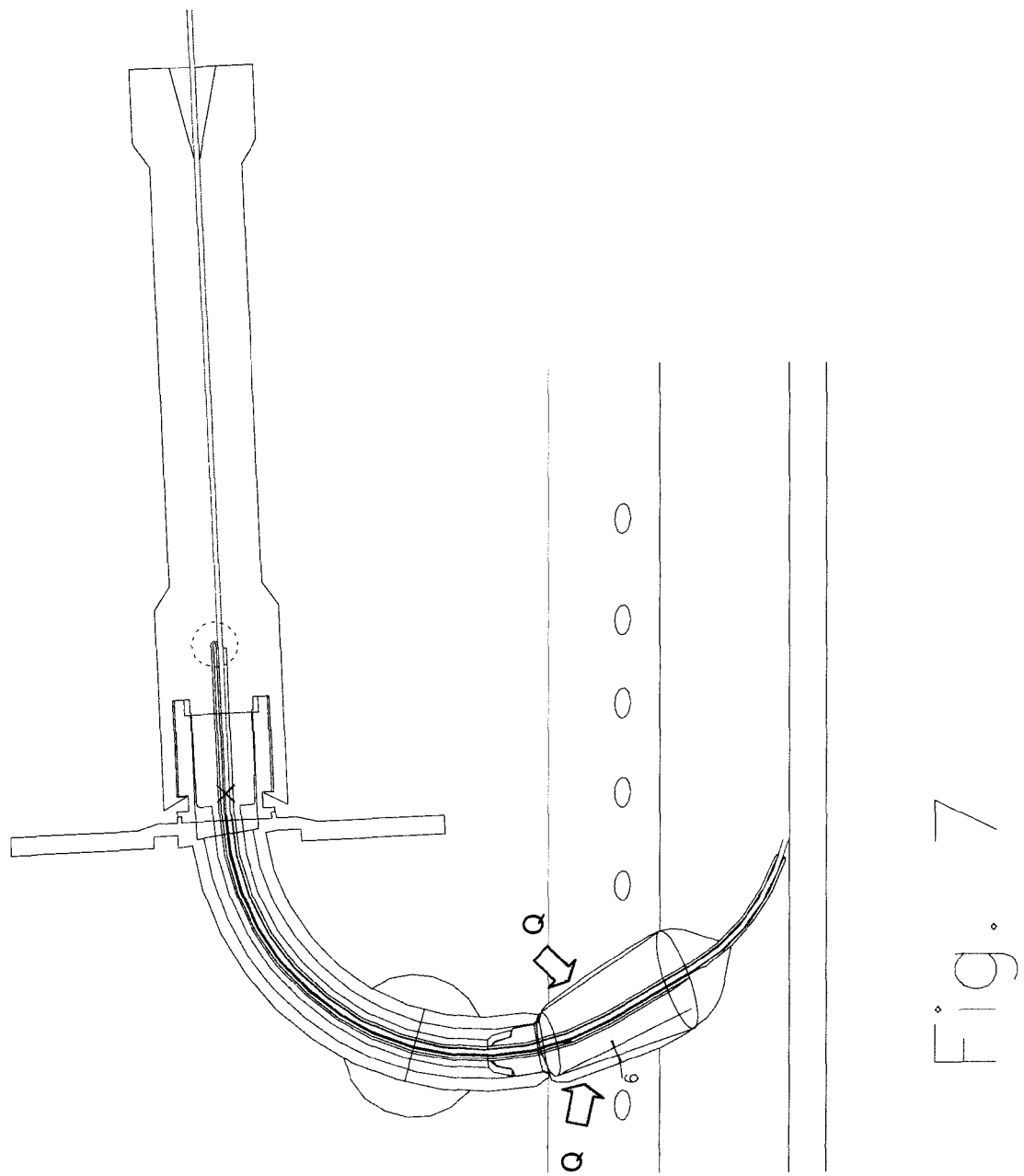
FIG. 7 represents a view of longitudinal section of the active portion active of the inflated balloon of the device when inserted in the tracheal wall, characterized by a reverse truncated cone.

The idea to build a dilator balloon with a truncated cone follows also the formula P=2 q tg alpha where alpha is determined in a rectangle triangle by the ratio between base (25-30 mm) and height, that at the end of the dilation phase will correspond to 1.5-2 mm, giving an angle of 4°-7° degrees for side, sufficient to produce a thrust to move forward the device in the trachea of 0.5-1, atmospheres (or Kilo) per square centimeter, when P is 6 atmospheres (FIG. 7, truncated cone with angle 5°-6° degrees, direction vector Q to inside). (P=Force for open the tracheal wall, Q=Resistance to open the wall)

The shape of the inflated balloon in the advancing phases of the device, will keep the aperture just formed open and dilated, with dimensions slightly larger than the tube itself to help the insertion of the tracheal tube.

The dilator balloon is made of a material capable to withstand shape and a pressure of 6-8 atmospheres without deformation. Examples are polymeric materials, as nylon.

The proximal part of the dilator balloon (11) enters 1-2 centimeters in the tracheostomy tube allowing the balloon once inflated to adhere perfectly and solidly to the tracheostomy tube and in the same way allowing to compact the intermediate part of the device, tighten between handle and balloon, giving robustness and support to the whole device (FIG. 1).

Figure 5:
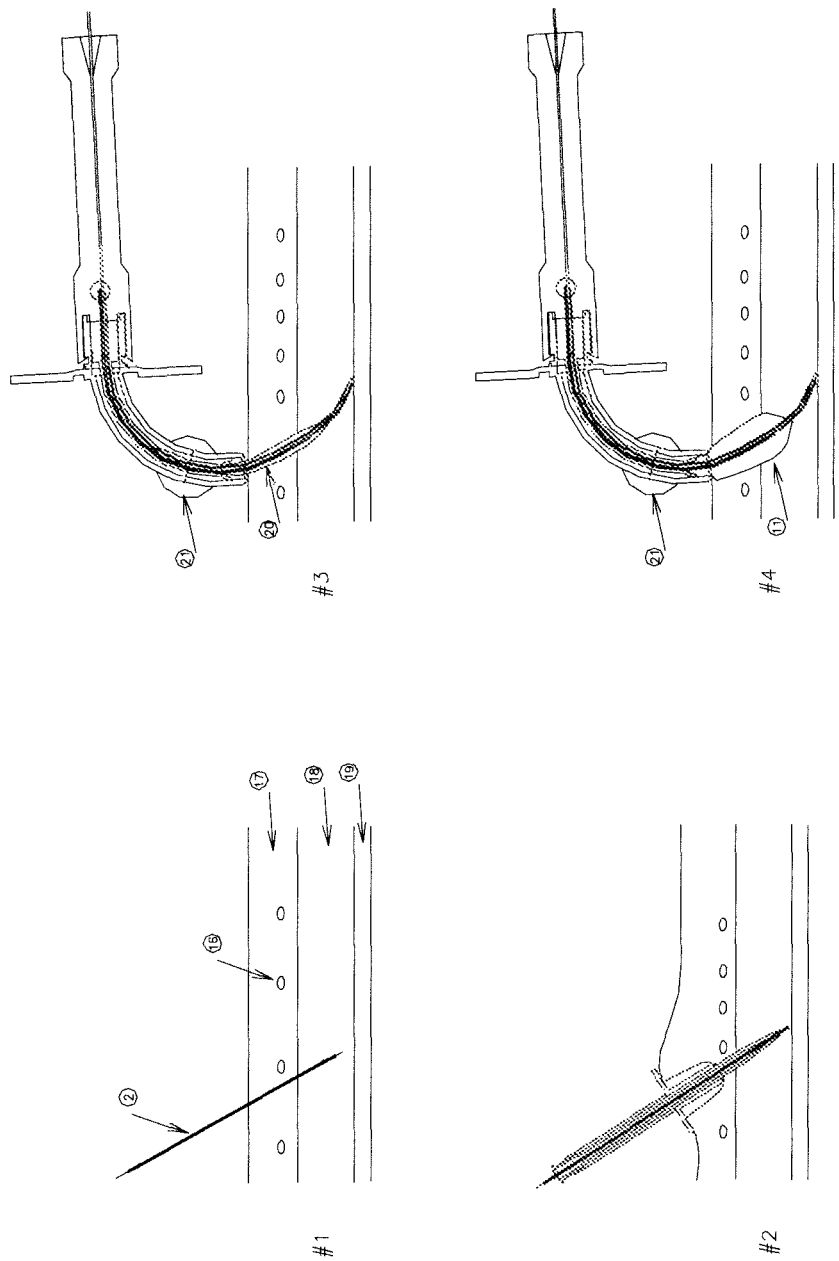
FIG. 5 represents description steps of the tracheostomy using the apparatus of the invention (steps #1 to #4)

The tracheostomy tube is grip firmly to the device (FIG. 1), thus allowing the device after the dilation phase to be used also as insertion device. Thanks to its shape of truncated cone (FIG. 7) the inflated balloon keeps the tracheal tissues compact, through the aperture, and develops a thrust for insertion of the tracheal tube. This allows to simplify the procedure, compared to other medical devices that requires the use of more tools to perform the same tasks. Thanks to its tapered shape in the intermediate part, once the tube has been inserted and the balloon is deflated, the handle is removed and the device can be easily withdrawn (FIG. 5-6 #5-6-7). The device performs the task in a way better than any other introducer device.

Figure 8:
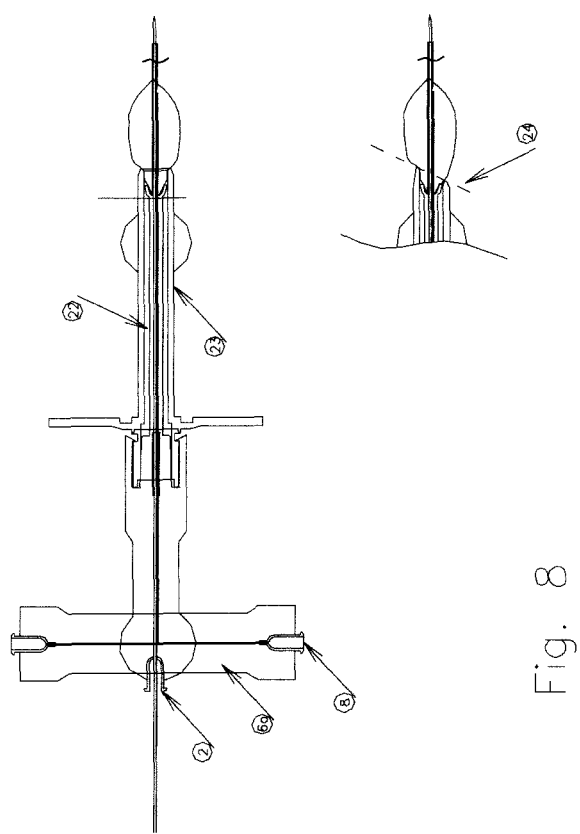
FIG. 8 represents a view of longitudinal section of an alternative embodiment of the device.

An alternative device is proposed (FIG. 8), allowing the insertion of a medical device like an armored silicone rubber tracheostomy tube armored (FIG. 8. n23). The armored tracheostomy tube is flexible and is carried onto a straight intermediate portion of the device (FIG. 8 n.22). The intermediate portion is made of plastic material like PVC and contains the tube for the wire guide (FIG. 8 n.2) as well as the balloon inflating tube that continue in the distal end of the device (FIG. 8). The structure in the intermediate part is sustained by four laminar elements (FIG. 8. n22) with angle of 45° starting from the handle in the proximal part and ending with a cup adherent to the dilator balloon. As shown in FIG. 8, the tip (24) of the tracheostomy tube, made of hard material (plastic material hydrophobic), is smoothing and flute spout shaped.

EXAMPLES OF APPLICATION

The procedure can be followed with the patient soothed, intubated and ventilated, with an automatic respirator and with a safe access of the airways, as well as in emergency situations without open airways. This procedure is addressed to physicians expert in reanimation and emergency techniques, or in any case competent in the management of aerial ducts. The patient must be supine and in a position correct for tracheostomy, when possible preferably with the neck hyperextended. The operating environment has to be prepared with sterilized cloths and skin disinfection; the vital functions have to be monitored. The procedure can be facilitated by an endoscopic control through the orotracheal tube, when present. The insertion of the device provided with the tracheal tube is preceded by the injection in the lumen between the tracheal rings, usually between the second and the third one (FIG. 5-6). This is made with a hollow needle 17 G×70millimeters/ 14×52, with metal internal bore, connected to a 10 ml Luer syringe; the air sucked up will confirm the correct access to the trachea. Once the tube is placed, the metallic needle is removed and a wire guide with J tip is inserted (FIG. 5 #1); this will be used as guidance to the following steps (FIG. 5-FIG. 6, FIG. 1, n.2-13).

Before introducing the device, a small dilator along the wire guide is introduced. This has a diameter of 4-5 millimeters, a length of 10-11 centimeters, included the handle of 6 cms (FIG. 2), with two small opposite scalpel blades (FIG. 2, particular n.1) positioned at 180 degrees and in drawing close to the hilt of the dilator (FIG. 2, particular n.3) it is made preferably of hydrophobic plastic material, and its role is to make a first small dilation, preparatory for the following one (FIG. 5, #2). This tool is used to facilitate the insertion of the uninflected balloon and to cause a quick opening of the tracheal aperture allowed by the precise incision along the wire guide (2) of the two blades on the tracheal rings. (FIG. 5, #2).

The following step is the insertion of the distal portion of the device, inclusive of tracheal tube, that is the uninflected dilator balloon, previously well lubricated (FIG. 5, #3, insertion of the uninflected dilator balloon of device provided with the tracheal tube). To inflate the balloon (FIG. 5 #4) with fluid a piston or screw syringe can be used, as well as a pump with pistol hilt. In order to guarantee a better safety to the device the tools can be provided with a pressure gauge and an overpressure valve. After starting the balloon inflation this will spread from inside the trachea will push the device with the tracheal tube against the tracheal rings, compressing the tracheal tissues between balloon and tube, the inflating pressure will dilate the tracheal aperture up to the maximum extension of the balloon (FIG. 5 #4). When the tracheal aperture is large enough to receive the tracheotomy tube, the dilator balloon is used as insertion device keeping the aperture open and dilated for the tracheal tube insertion (FIG. 5 #5). Moreover, the truncated cone shape will reduce to a minimum the effort needed for the advancing phase, reducing the attrition to a minimum and maintaining a thrust for insertion proportional to the angle of inclination at the base of the cone (FIG. 7). Once the tube is inserted, the balloon is deflated (FIG. 6 #6), the handle is rotated of 180 degrees and the small flexible hooked arms (7) removed from the hook-up with the proximal part of the tracheal tube (4). The device, inclusive of the wire guide may be taken out of the tracheal tube (FIG. 6 #7). After the correct placement of the tube, this is fixed by neck plate (FIG. 1, 15).

The invention claimed is:

1. A tracheostomy device, comprising:
   a handle;
   an inflating tube;
   a wire guide tube;
   an intermediate portion to sustain the inflating tube and the wire guide tube;
   a tracheal tube surrounding the intermediate portion; and
   a dilating balloon, being inflatable through the inflating tube, the balloon having a proximal portion and a distal portion, each of the balloon, the proximal portion of the balloon and the distal portion of the balloon having a respective proximal end and a respective distal end, the distal end of the proximal portion and the proximal end of the distal portion being separated by a major diameter, the proximal portion being active during dilation such that the proximal portion of the balloon forms a reverse truncated cone shape,
   wherein, when the balloon is inflated, the balloon has a base diameter at the major diameter which is larger than the proximal portion of the balloon,
   the shape of the balloon is tightly connected to the tracheal tube such that the proximal portion of the balloon is partially inside a lumen of the tracheal tube, and the proximal portion of the balloon outside the tracheal tube is larger in diameter than the tracheal tube such that, when the balloon is inflated, the dilating balloon causes a thrust to move forward the device in a trachea of a patient,
   a distal portion of the inflating tube is connected to the distal end of the balloon; and
   the distal portion of the balloon has a base diameter at the major diameter which is larger than a base diameter at a remainder of the distal portion of the balloon when the balloon is inflated; wherein the inflating tube has an end forming an opening through which a dilation force is first delivered to the distal portion of the balloon to inflate the balloon; wherein, outside of the tracheal tube, the balloon is devoid of a tubular section of constant diameter when the balloon is inflated.

2. The tracheostomy device according to claim 1, wherein a distal region of the handle is connected to a proximal end of the tracheal tube by a twist-lock connector or a connector with two hooked arms.

3. The tracheostomy device according to claim 1, wherein the handle handgrip is placed across the handle in a "T" shape.

4. The tracheostomy device according to claim 1, wherein the intermediate portion sustains and carries the tracheal tube.

5. The tracheostomy device according to claim 1, wherein the intermediate portion is curved.

6. The tracheostomy device according to claim 1, wherein the intermediate portion is straight.

7. The tracheostomy device according to claim 1. wherein the balloon has a shape of two adjacent, back-to-back cones when the balloon is inflated.

8. The tracheostomy device according to claim 1, wherein the balloon has a shape of a proximal, truncated cone directly connected to a distal cone when the balloon is inflated.

9. The tracheostomy device according to claim 1, wherein, outside the tracheal tube, the balloon has a non-constant diameter along its entire length when the balloon is inflated.

10. An apparatus for tracheostomy, comprising:
    the tracheostomy device according to claim 1; and
    a small dilator to facilitate an introduction of the device into the patient comprising, at an outer part, two opposite scalpel blades.

11. A method for performing a non traumatic tracheostomy with the apparatus according to claim 10, comprising the steps of:
    a) forming a punctured opening in the tracheal wall with a needle;
    b) inserting a wire guide through the needle bore and withdrawing the needle;
    c) inserting the small dilator
    d) blading along the wire guide across the tracheal wall;
    e) inserting the apparatus along the wire guide across the tracheal wall with the tracheostomy tube hooked to the handle and positioning the deflated balloon in the internal wall of the trachea;
    f) inflating the balloon, having the inflation start from its distal end of the balloon to get dilation of said punctured opening by the pressure of the inflated balloon on the tracheal wall from inside the trachea outwards;
    g) having the tracheal wall dilated, inserting the tracheostomy tube inside the trachea;
    h) deflating the balloon and withdraw the apparatus from the tracheostomy tube.

12. The apparatus according to claim 10, wherein the two scalpel blades are positioned at 180 degrees relative to each other.

* * * * *

UNITED STATES PATENT AND TRADEMARK OFFICE
CERTIFICATE OF CORRECTION

PATENT NO.        : 8,757,161 B2
APPLICATION NO.   : 12/441815
DATED             : June 24, 2014
INVENTOR(S)       : Romano Guerra Page 1 of 1

It is certified that error appears in the above-identified patent and that said Letters Patent is hereby corrected as shown below:

On The Title Page,

Item (30), Foreign Application Priority Data:
please delete "GO20060001 U" and insert --GO2006U00001--

Item (74), please delete "LLP" and insert --LLC--

Signed and Sealed this
Sixth Day of January, 2015

Michelle K. Lee
*Deputy Director of the United States Patent and Trademark Office*